United States Patent [19]

Nemeth

[11] 4,111,205
[45] Sep. 5, 1978

[54] REFASTENABLE DIAPER TAB CLOSURE

[75] Inventor: Suzette B. Nemeth, Painesville, Ohio

[73] Assignee: Avery International Corporation, San Marino, Calif.

[21] Appl. No.: 770,646

[22] Filed: Feb. 22, 1977

[51] Int. Cl.² .............................................. A61F 13/16
[52] U.S. Cl. ...................................... 128/284; 128/287
[58] Field of Search ................................ 128/284, 287; 428/40–43, 352, 354, 121, 124; 24/DIG. 11

[56] References Cited

U.S. PATENT DOCUMENTS

| | | | |
|---|---|---|---|
| 3,862,634 | 1/1975 | Small | 128/284 |
| 3,874,386 | 4/1975 | Kozak | 128/287 |
| 4,020,842 | 5/1977 | Richman et al. | 128/287 |

Primary Examiner—John D. Yasko
Attorney, Agent, or Firm—McNenny, Pearne, Gordon, Gail, Dickinson & Schiller

[57] ABSTRACT

A web construction of diaper tab stock is provided for separation into diaper tabs of the refastenable type wherein a minor part of the tab transfers from one part of the diaper to another incident to the first cycle of fastening and unfastening. The release-coated substrate face which substitutes for a liner does not stay with the main part of the tab structure during such cycle but instead transfers with the minor part of the tab structure. The diaper tab stock is suited to low cost production and to high speed dispensing on automatic equipment by diaper manufacturers.

4 Claims, 5 Drawing Figures

REFASTENABLE DIAPER TAB CLOSURE

This invention relates to laminate web comstructions of linerless, refastenable tab stock of the kind adapted to be supplied to a diaper manufacturer and to be separated by the manufacturer into individual diaper tab constructions and applied to individual diapers, usually two tabs to a diaper. By "linerless" is meant the absence of any adhesive-protecting liner of release paper or the like that has to be separately disposed of by the person applying the diaper, either when the diaper is originally applied or when the diaper is reclosed after checking for continuing dryness and non-soiling. By refastenable is meant a diaper tab which can be fastened by exposing and applying an adhesive face and refastened by exposing and applying a "fresh" second adhesive face.

Application Ser. No. 624,870, filed Oct. 23, 1975 now U.S. Pat. No. 4,020,842, of common assignee, discloses a diaper tab of the linerless refastenable type wherein a minor part of the tab transfers from one part of the diaper to another incident to the first cycle of fastening and unfastening of the diaper. The same two substrates form (1) the free or "outboard" end of the tab and (2) the manufacturers' joint of permanently fastened "inboard" end of the tab. The second of these two substrates is slit into inboard and outboard portions so that, when the "outboard" end of the first substrate is lifted to initially unfasten a diaper fastened by the tab, a minor part of the tab comprising the "outboard" end of the second substrate is thereby separated from and left behind the main portion of the tab structure, completing the transfer referred to above, and thereby adhesive on the outboard end of the first substrate is exposed to be used for refastening. Prior to such initial unfastening, the adhesive on the outboard end of the first substrate is protected by the second substrate which carries first substrate release means on its adjacent surface. However the adhesive on the outboard end of the second substrate must also be protected prior to use in originally fastening the diaper on an infant. In order that the construction may be linerless, the second substrate is folded across second substrate release means carried by a third substrate on the manufacturers' joint or permanently fastened inboard end of the tab, and is releasably supported thereon and on the inboard side of the slit. Then when the diaper is originally fastened on an infant, the second substrate is unfolded back off the second substrate release means and across the slit to expose the second substrate adhesive on the outboard end, leaving the second substrate release means still at the inboard end where it thereafter remains with the main portion of the tab structure during closing, opening and reclosing of the tab without any requirement for separate disposal.

In the present invention the reclosable construction is simplified by changing the arrangement so that the second substrate release means no longer remains with the main part of the tab construction during opening and reclosing. Instead the second liner release means is arranged in such a way that it transfers and remains with the left-behind part of the tab structure when the fastened diaper is first unfastened. The second substrate release means is carried on the second substrate itself, and is located outboard of both the manufacturers' joint and the slit. The result is a linerless refastenable diaper tab formed of two-substrate stock rather than three-substrate stock.

U.S. Pat. No. 3,943,609 to Egan discloses a diaper tab wherein release means is provided on the outboard end of a tab, but the tab is not of a refastenable type and there is no arrangement for leaving behind the release means with part of the tab structure when the fastened diaper is first unfastened.

Importantly, as in the case of the tab stock shown in the aforesaid application of common assignee, the diaper tab stock of the present invention can be manufactured by being formed of initially flat but flexible layers formed in long passes along the machine direction of a coating and laminating line, and the stock is fabricatable completely by web coating, slitting and web-to-web laminating operations and without the necessity for folding operations, and, when cut into short lengths and folded and applied to diapers by high speed dispensing equipment of a diaper manufacturer, the stock provides conveniently usuable linerless refastenable diaper tabs, but of a simplified design.

In the drawings, the thicknesses of the webs and coatings are greatly exaggerated.

Figure 1:
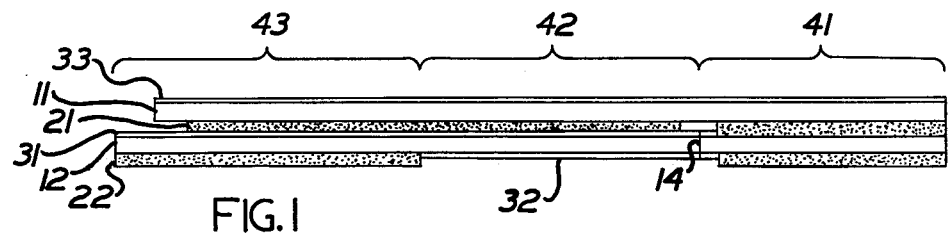
FIG. 1 is a schematic transverse elevation of diaper tab stock constructed according to the invention and then cut transversely to machine direction (machine direction being into the paper) into an individual laminate.

As seen in FIG. 1, the web construction comprises a first substrate 11, extending, transversely to machine direction, along first, second and third length portions 41, 42 and 43 respectively. The first substrate bears first substrate adhesive 21 on its underside. Preferably the adhesive 21 is interrupted in the vicinity of the boundary between the first and second length portions and stops short of the free end of said substrate at the third length portion, as seen in FIG. 1. The three length portions are preferably approximately equal in length.

A second substrate 12 also extends along the length portions 41, 42 and 43. The second substrate bears the second substrate adhesive 22 on its underside. The second substrate adhesive 22 extends along the first and third length portions 41 and 43, as shown.

The second substrate is slit or divided along the machine direction in the region of adjacency of the first and second length portions, as indicated at 14. The second substrate 12 carries first substrate release means 31 on its upper side coextensively with the first substrate adhesive 21 at the second and third length portions. The second substrate also carries second substrate release means 32 on its underside along the second length portion 42.

The construction in the form so described and shown in FIG. 1 can be supplied to a diaper manufacturer as a self-wound roll of diaper tab stock. For this purpose an additional release coating 33 is provided on which the second substrate adhesive 22 is received when the roll of tab stock is self-wound.

Figure 2:
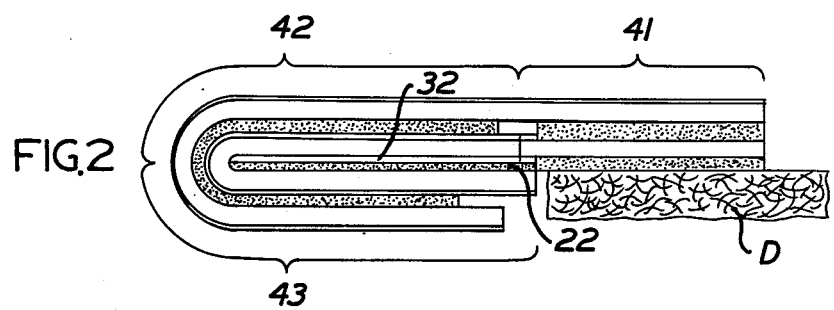
FIG. 2 is a view of the laminate shown in FIG. 1 as folded and fastened at one edge of one portion of a diaper by the diaper manufacturer.

The diaper tab manufacturer cuts the roll of diaper tab stock transversely and rolls the third and second length portions of the tab together and applies the first length portion to the diaper D, as seen in FIG. 2. The adhesive 22 on the third length portion 43 is thereby protected by being positioned against the second substrate release means 32.

Figure 3:
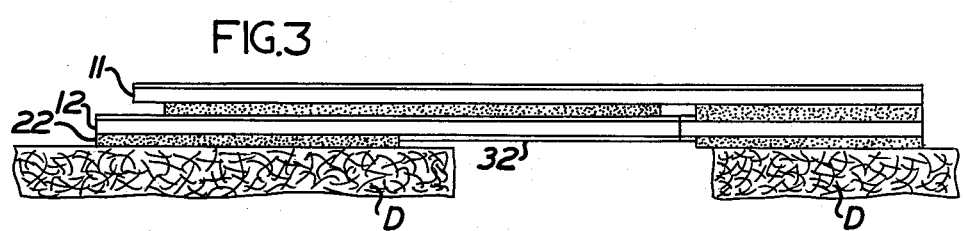
FIG. 3 is a view of the same laminate, now unfolded to form a tab which is joined to another portion of the diaper.
Figure 4:
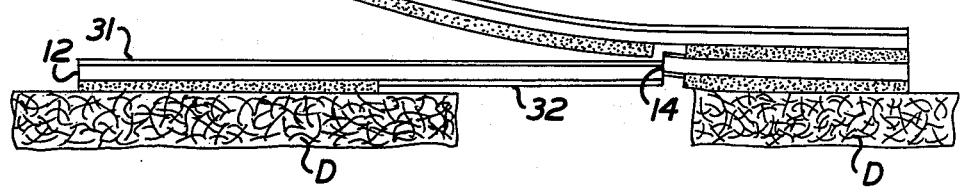
FIG. 4 is a view similar to FIG. 3 showing the configuration of the parts at the moment of unfastening of the diaper tab following its initial fastening.

When the diaper is first applied, the third length portion is unfolded to expose the second substrate adhesive 22 which is then applied against another part of the diaper D, as seen in FIG. 3. Subsequently, when the diaper is first unfastened, the first substrate can be released from the second substrate at the second and third length portions in the manner illustrated in FIG. 4. This involves peeling back the first substrate adhesive 21 from the first substrate release means 31. When the peel-back progresses to the vicinity of the slit 14, the peel-back force ends and the two joined parts of the diaper come apart. It will be therefore noted that, during the cycle of fastening and unfastening the diaper, the minor portion of the tab which consists of the second and third length portions of the second substrate 12 transfers from one part of the diaper to the other and carries with it the second substrate release means 32, such latter release means being the release means that substitutes for a liner and hence renders the construction linerless. Accordingly it will be understood that the release-coated substrate face which substitutes for a liner and hence which renders the construction "linerless" does not stay with the main part of the tab structure during the fastening and unfastening cycle but instead transfers with the minor portion of the tab structure to thereafter remain permanently associated with the joined part of the diaper that did not originally support the tab. Thus the substitute for a liner continues to be associated with the diaper, but on another part than that which it was originally associated with. The construction remains "linerless" without any necessity for disposing of a protective liner, but this is accomplished by the just-described transfer rather than by providing a liner substitute on or associated with one of the faces of the part of the diaper with which the tab is originally associated.

Figure 5:
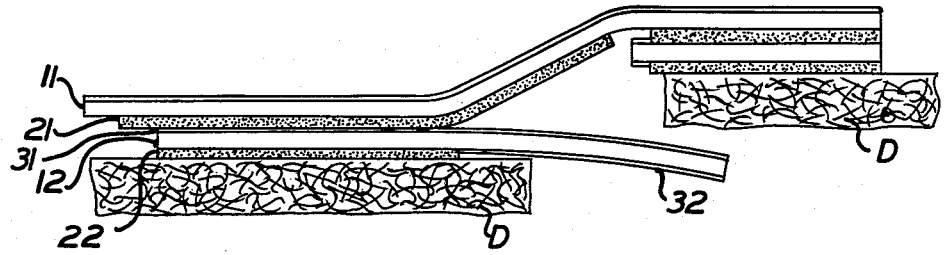
FIG. 5 is a similar view showing refastening of the diaper tab.

When the diaper is to be refastened, the diaper is pulled together and the first substrate adhesive 21 is used to refasten the diaper either against the release coat 31 as shown in FIG. 5, or against the surface of the diaper itself.

The invention is not limited to the precise details of the construction shown, but is defined by the following claims.

What is claimed is:

1. A diaper having a linerless refastenable two-substrate diaper tab formed of diaper tab stock comprising a two-substrate web construction made up of initially flat but flexible layers suitable to be formed in long passes along the machine direction of a coating and laminating line and to be rolled up for storage and shipment, and unrolled for use by diaper manufactures, and fabricatable completely by web coating, slitting and web-to-web laminating operations and without the necessity for folding operations, and suitable for high speed dispensing on automatic equipment, said tab including a first substrate extending, transversely to machine direction, along first, second and third length portions and bearing first substrate adhesive on its underside, a second substrate extending along said first, second and third length portions and bearing second substrate adhesive on its underside, said second substrate adhesive extending at least partially along at least said first and third length portions, said second substrate being slit or divided along the machine direction in the region of adjacency of said first and second length portions, said second substrate carrying first substrate release means on its upper side at least co-extensively with any first substrate adhesive at the second and third length portions and carrying second substrate release means on its underside along said second length portion whereby said third and second length portions of said second substrate can be folded together as by a diaper manufacturer, to protect the second substrate adhesive on said third length portion and can then be unfolded to freshly expose said adhesive, as upon fastening of the diaper, and subsequently, as upon unfastening of the diaper, said first substrate can be peeled back from said second substrate at said second and third length portions to freshly expose part of said first substrate adhesive for subsequent refastening of the diaper.

2. A construction as in the preceding claim in which said first substrate adhesive extends at least partially along at least said first and third length portions.

3. A construction as in the preceding claim in which said first substrate adhesive extends at least partially along all three of said length portions.

4. A construction as in claim 3 in which said first substrate adhesive is interrupted in the vicinity of the boundary between the first and second length portions and stops short of the free end of said first substrate at the third length portion.

* * * * *